US012622999B2

(12) United States Patent (10) Patent No.: US 12,622,999 B2
Choung et al. (45) Date of Patent: May 12, 2026

(54) PCL PATCH TISSUE REGENERATION SCAFFOLD AND METHOD FOR MANUFACTURING SAME

(71) Applicant: AJOU UNIVERSITY INDUSTRY-ACADEMIC COOPERATION FOUNDATION, Suwon-si (KR)

(72) Inventors: Yun-Hoon Choung, Seoul (KR); Jong Hoon Chung, Seoul (KR); Hoon Seonwoo, Seoul (KR); Kyoung-Je Jang, Seoul (KR); Beomyong Shin, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 40 days.

(21) Appl. No.: 18/370,878

(22) Filed: Sep. 21, 2023

(65) Prior Publication Data

US 2024/0009349 A1 Jan. 11, 2024

Related U.S. Application Data

(63) Continuation of application No. 16/317,028, filed as application No. PCT/KR2017/002262 on Mar. 2, 2017, now abandoned.

(30) Foreign Application Priority Data

Jul. 12, 2016 (KR) ........................ 10-2016-0088071
Feb. 10, 2017 (KR) ........................ 10-2017-0018835

(51) Int. Cl.
*A61L 27/18* (2006.01)
*A61F 2/18* (2006.01)
(Continued)

(52) U.S. Cl.
CPC ............... *A61L 27/18* (2013.01); *A61L 27/54* (2013.01); *C08G 63/08* (2013.01); *D01D 5/003* (2013.01);
(Continued)

(58) Field of Classification Search
CPC ...... A61L 27/18; A61L 27/54; A61L 2400/12; A61L 2430/14; A61L 27/26; A61L 27/56;
(Continued)

(56) References Cited

U.S. PATENT DOCUMENTS

2009/0246259 A1 10/2009 Kita et al.
2016/0017279 A1 1/2016 Cha et al.
2016/0228606 A1 8/2016 Danti et al.

FOREIGN PATENT DOCUMENTS

JP 5424561 B2 2/2014
KR 10-2008-0013224 A 2/2008
(Continued)

OTHER PUBLICATIONS

Golin, A. (Dissertation. Humidity effect on the structure of electrospun core-shell PCL-PEG fibers for tissue regeneration applications. The University of Western Ontario (Canada), 2014. (Year: 2014).*
(Continued)

*Primary Examiner* — Sharmila G Landau
(74) *Attorney, Agent, or Firm* — Revolution IP, PLLC

(57) ABSTRACT

Disclosed is a method of treating a chronic tympanic perforation with a PCL patch tissue regeneration scaffold comprising preparing solution by adding polycaprolactone (PCL) and an acid to an organic solvent; preparing an electrospinning solution by adding a growth factor to the solution and stirring; collecting nanofibers arranged in a spindle shape on a collector by connecting the electrospinning solution prepared to a syringe pump and operating the
(Continued)

electrospinning device; and administering the PCL patch tissue regeneration scaffold to a subject.

2 Claims, 9 Drawing Sheets

(51) Int. Cl.

| | | |
|---|---|---|
| *A61L 27/54* | (2006.01) | |
| *C08G 63/08* | (2006.01) | |
| *D01D 5/00* | (2006.01) | |

(52) U.S. Cl.
CPC ........... *A61F 2/18* (2013.01); *A61F 2002/183* (2013.01); *A61F 2240/001* (2013.01); *A61L 2400/12* (2013.01); *A61L 2430/14* (2013.01); *D10B 2509/00* (2013.01)

(58) Field of Classification Search
CPC ... A61L 27/58; A61L 2300/414; C08G 63/08; D01D 5/003; D01D 5/0076; A61F 2/18; A61F 2002/183; A61F 2240/001; A61F 13/00; D10B 2509/00; C08L 67/04; D01F 6/92; D01F 6/625
See application file for complete search history.

(56) References Cited

FOREIGN PATENT DOCUMENTS

| KR | 10-2012-0103773 A | 9/2012 |
|---|---|---|
| KR | 10-2015-0084519 A | 7/2015 |
| KR | 10-1636778 B1 | 7/2016 |
| WO | 2015-040554 A1 | 3/2015 |

OTHER PUBLICATIONS

"Concentration as %." E-Safe Anaesthesia, e-safe-anaesthesia.org/sessions/17_03/d/ELFH_Session/451/tab_627.html. Accessed Jul. 16, 2025. (Year: 2025).*
Sawano, A. et al. (2002). "Lateral Propagation of EGF Signaling after Local Stimulation is Depedent on Receptor Density." Developmental Cell, vol. 3, 245-257. (Year: 2002).*
Zhang, Y. Z. et al. (2006). "Coaxial Electrospinning of (Fluorescein Isothiocyanate-Conjugated Bovine Serum Albumin)-Encapsulated Poly(-caprolactone) Nanofibers for Sustained Release." Biomacromolecules, vol. 7, 1049-1057. (Year: 2006).*
Feng, B. et al. (2012). "Acetic-Acid-Mediated Miscibility towards Electrospinning Homogenous Composite Nanofibers of GT/PCL." Biomacromolecules, vol. 13, 3917-3925. (Year: 2012).*
Ji, W. et al. (2010). "Fibrous scaffolds loaded with protein prepared by blend or coaxial electrospinning" Acta Biomaterialia, 6, 4199-4207. (Year: 2010).*
International Search Report for PCT/KR2017/002262 mailed Jun. 27, 2017 from Korean Intellectual Property Office.
Ji et al. Pharm Res (2011) 28: 1259-1272 (Year: 2011).
Montero, R. Dissertation, "Design of electrospun gelatin based scaffolds with controlled biological and architectural cues for therapeutic angiogenesis", University of Miami, 2012 (Year: 2012).
Repanas etal. Sch. Acad. J. Biosci., Feb. 2016; 4(2):149-153 (Year: 2016).
Jang et al. International Journal of Pediatric Otorhinolaryngology 78 (2014) 2237-2243. (Year: 2014).
Park et al. Polym Int 56:1361-1366, 2007. (Year: 2007).

* cited by examiner

[FIG. 1]
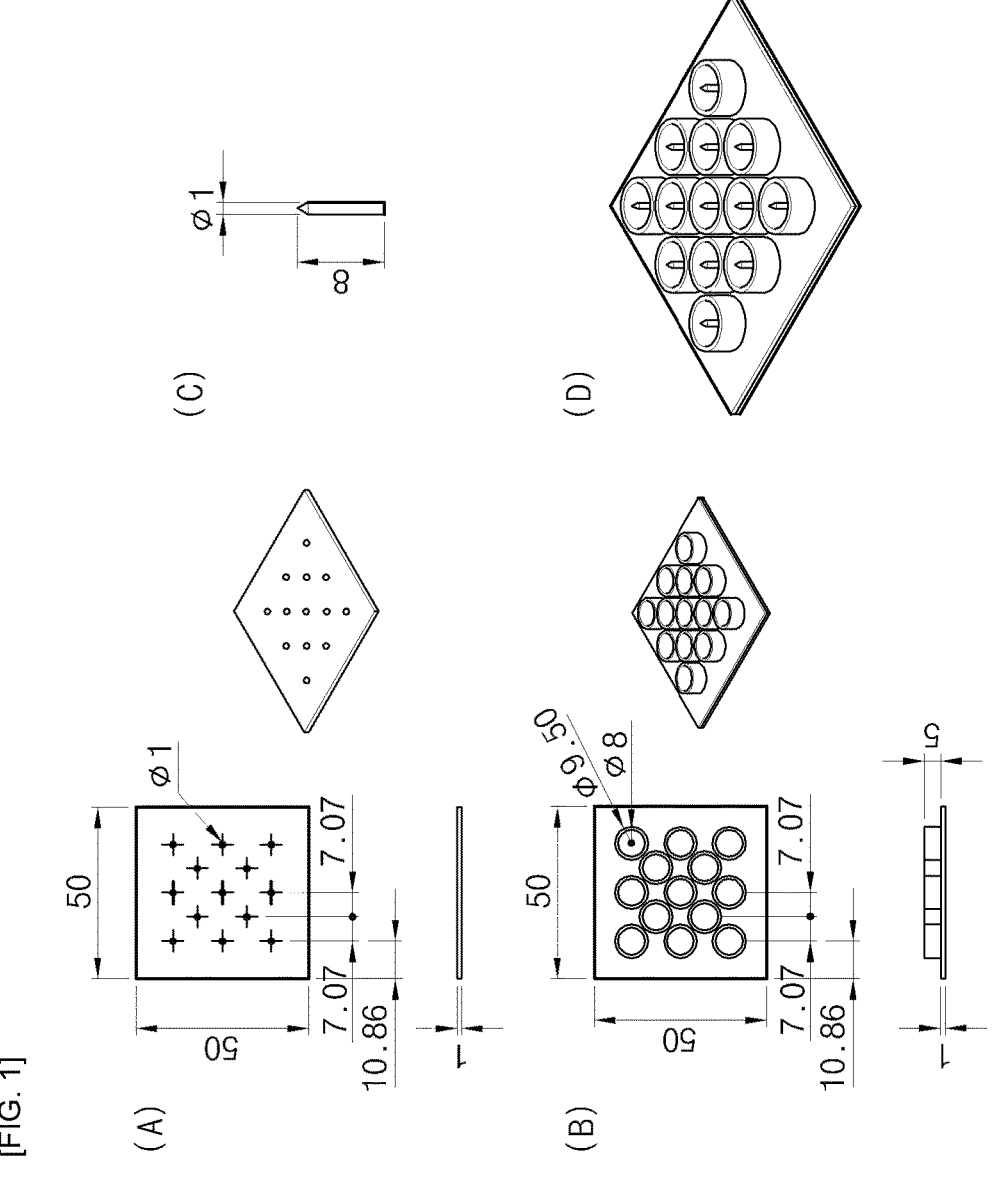

[FIG. 2]
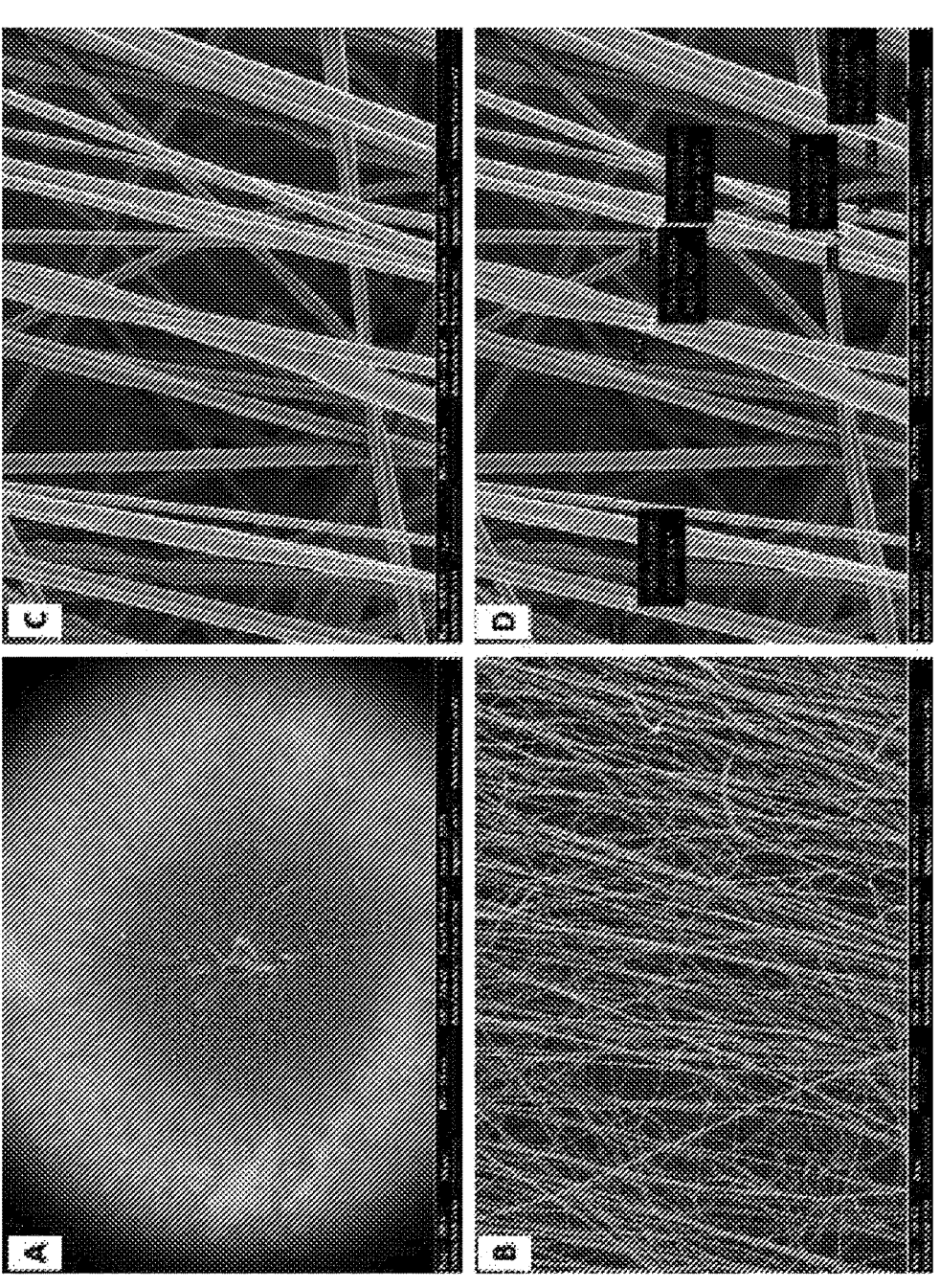

[FIG. 3]
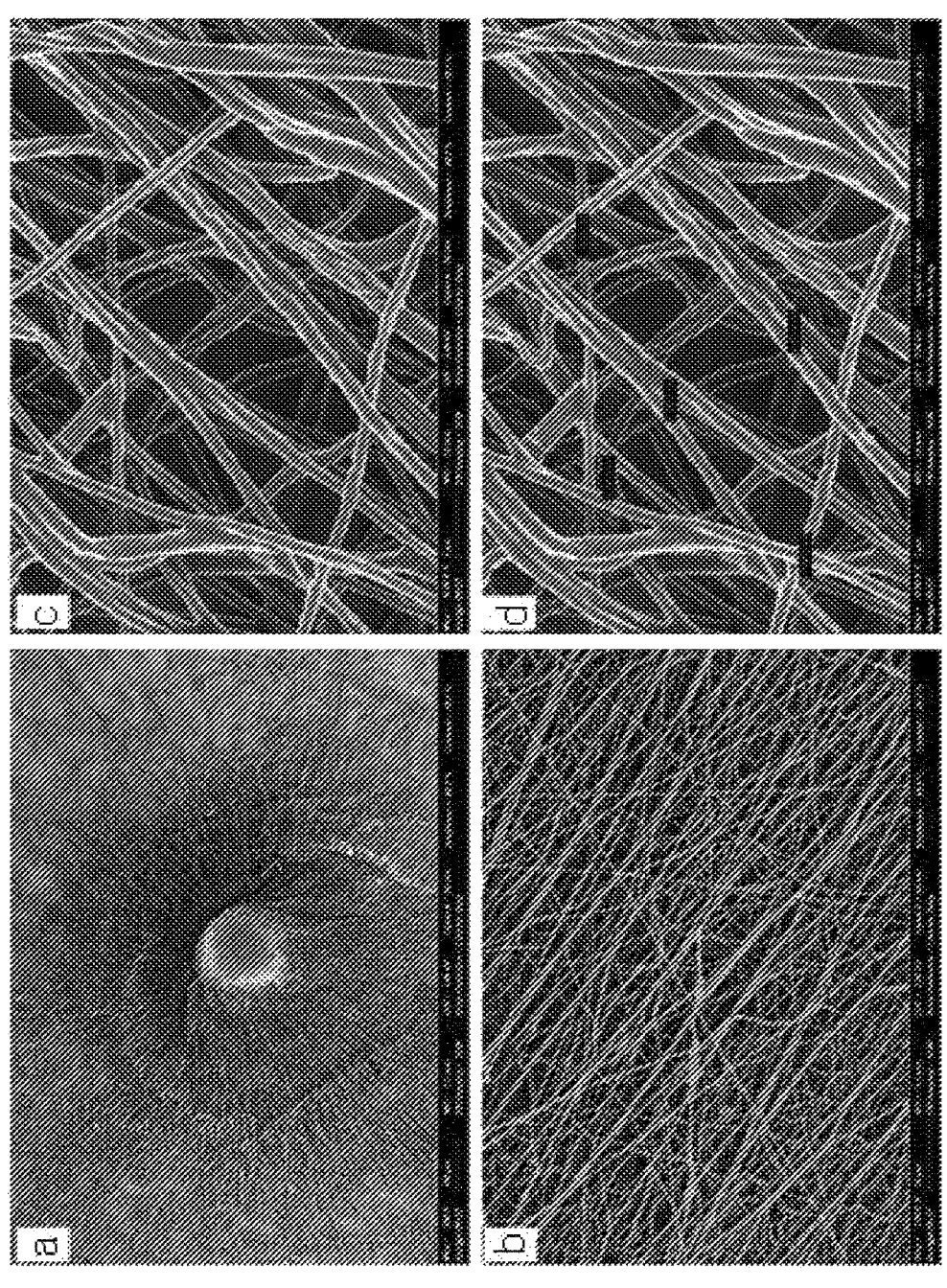

[FIG. 4]
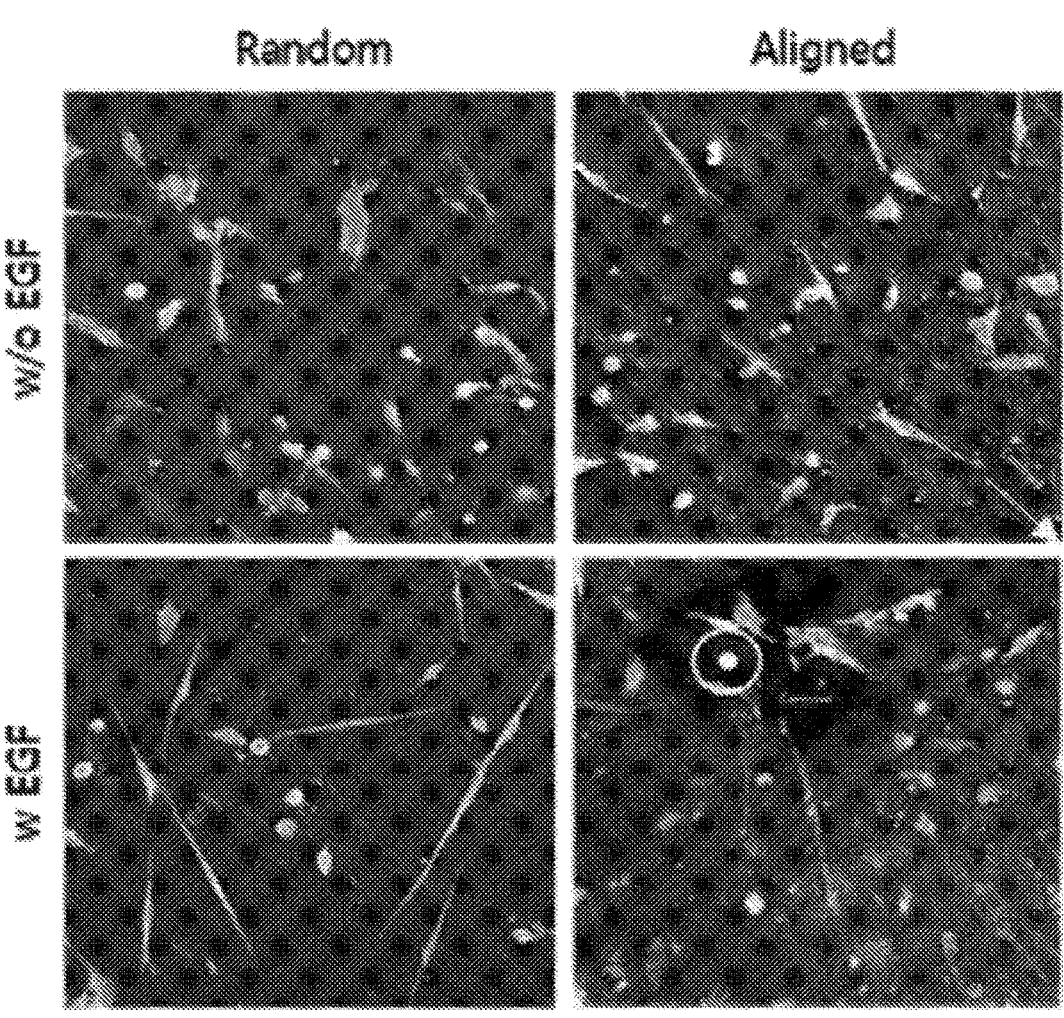

[FIG. 5a]
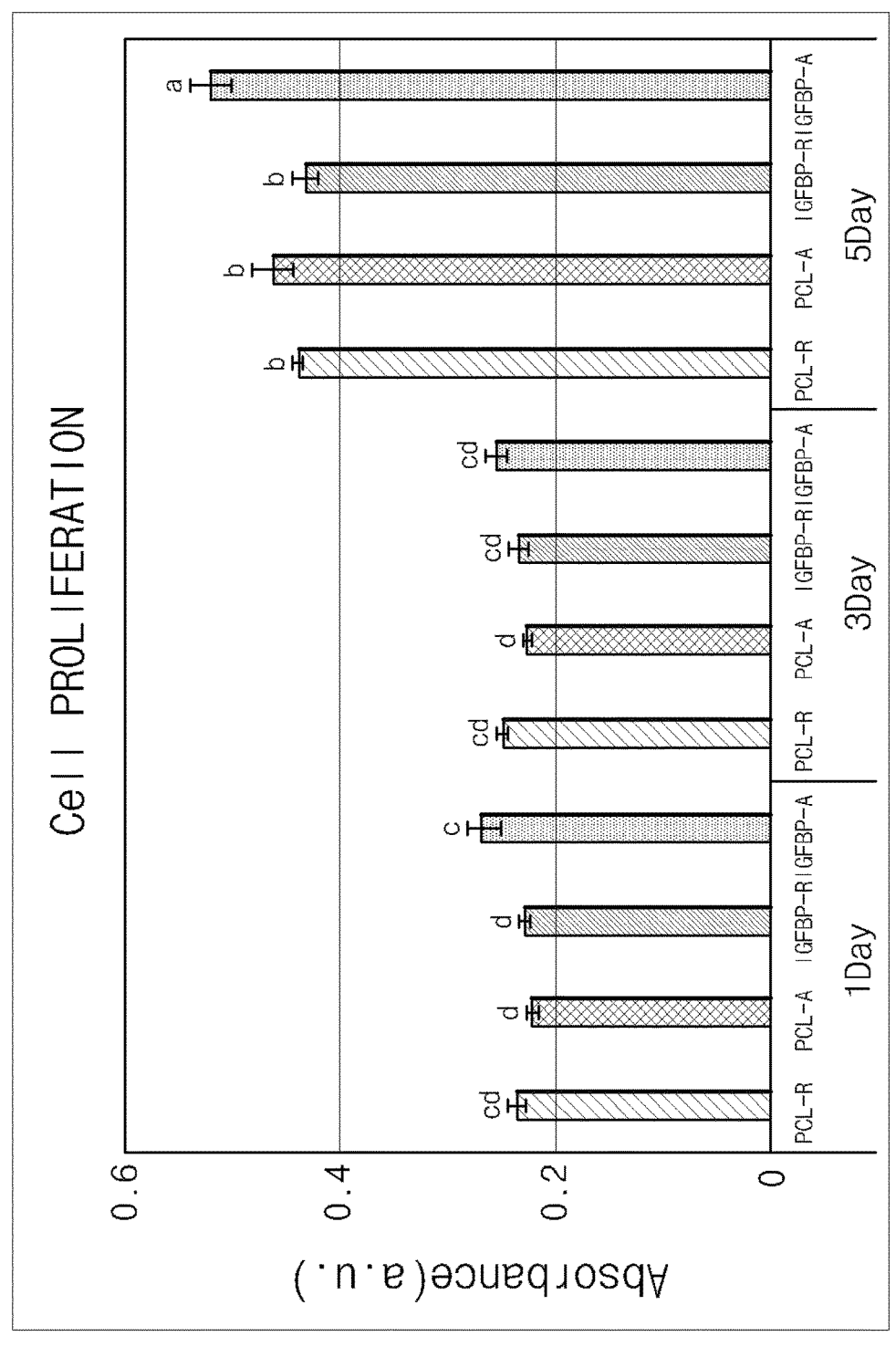

[FIG. 5b]
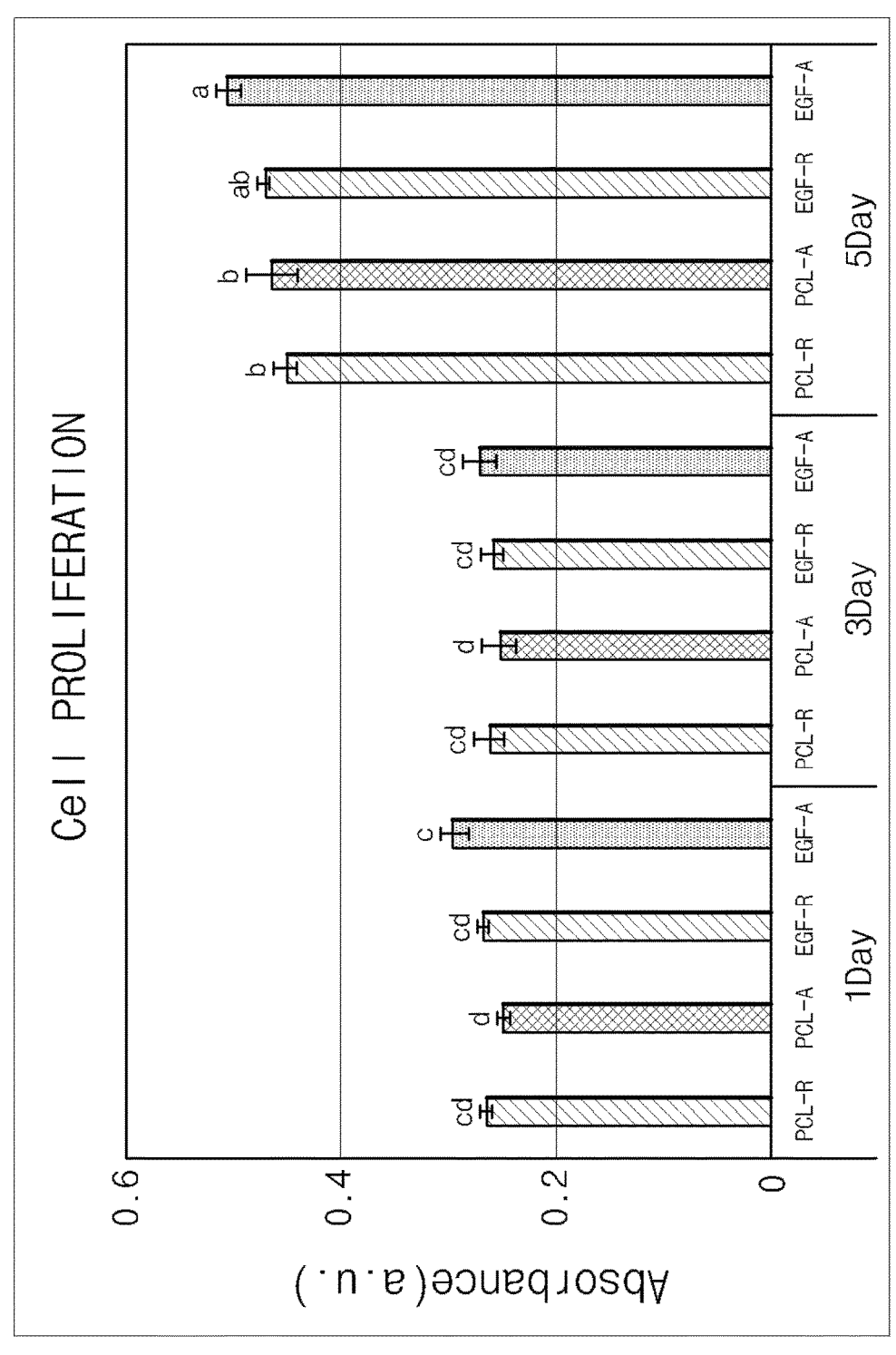

[FIG. 6]
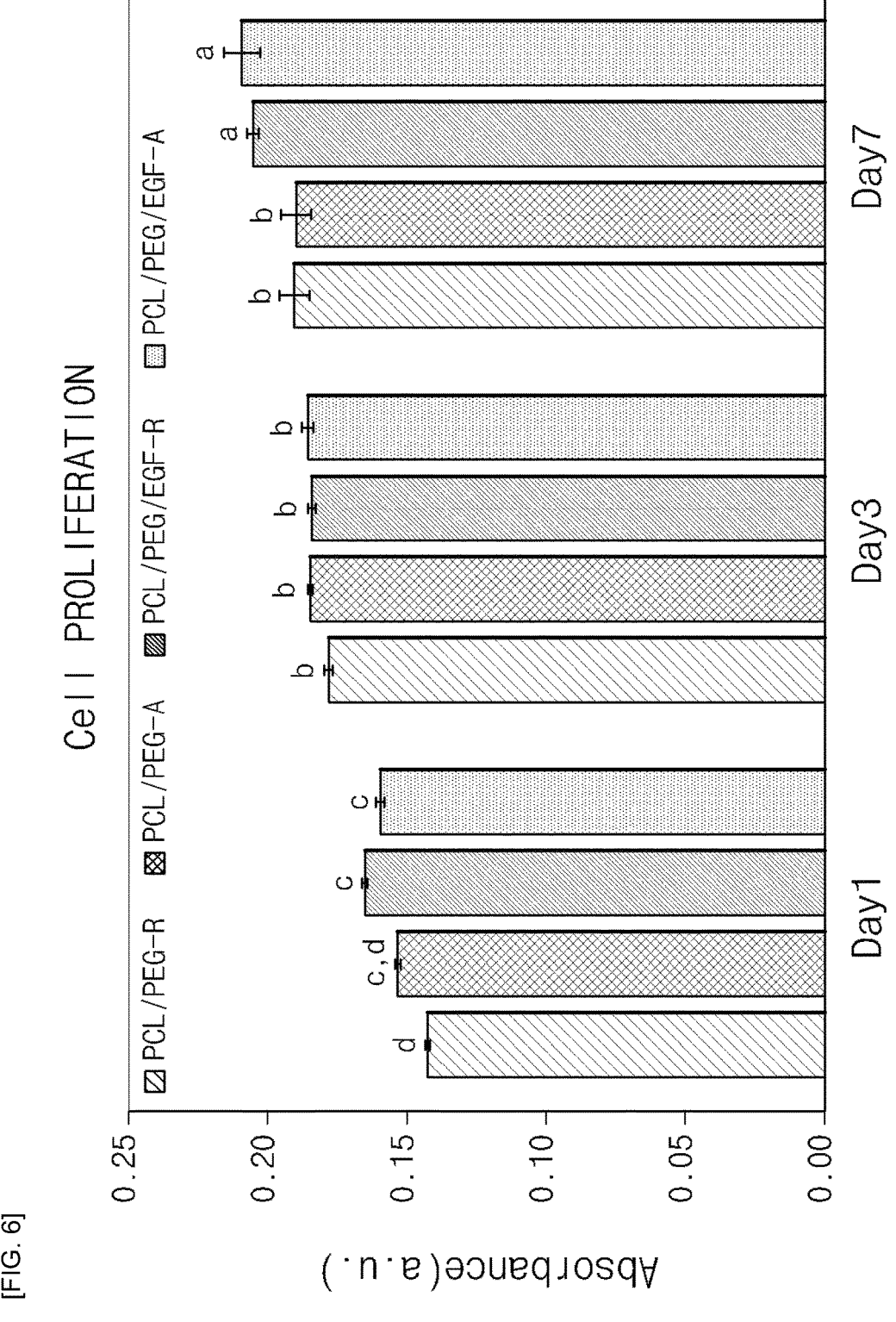

[FIG. 7]

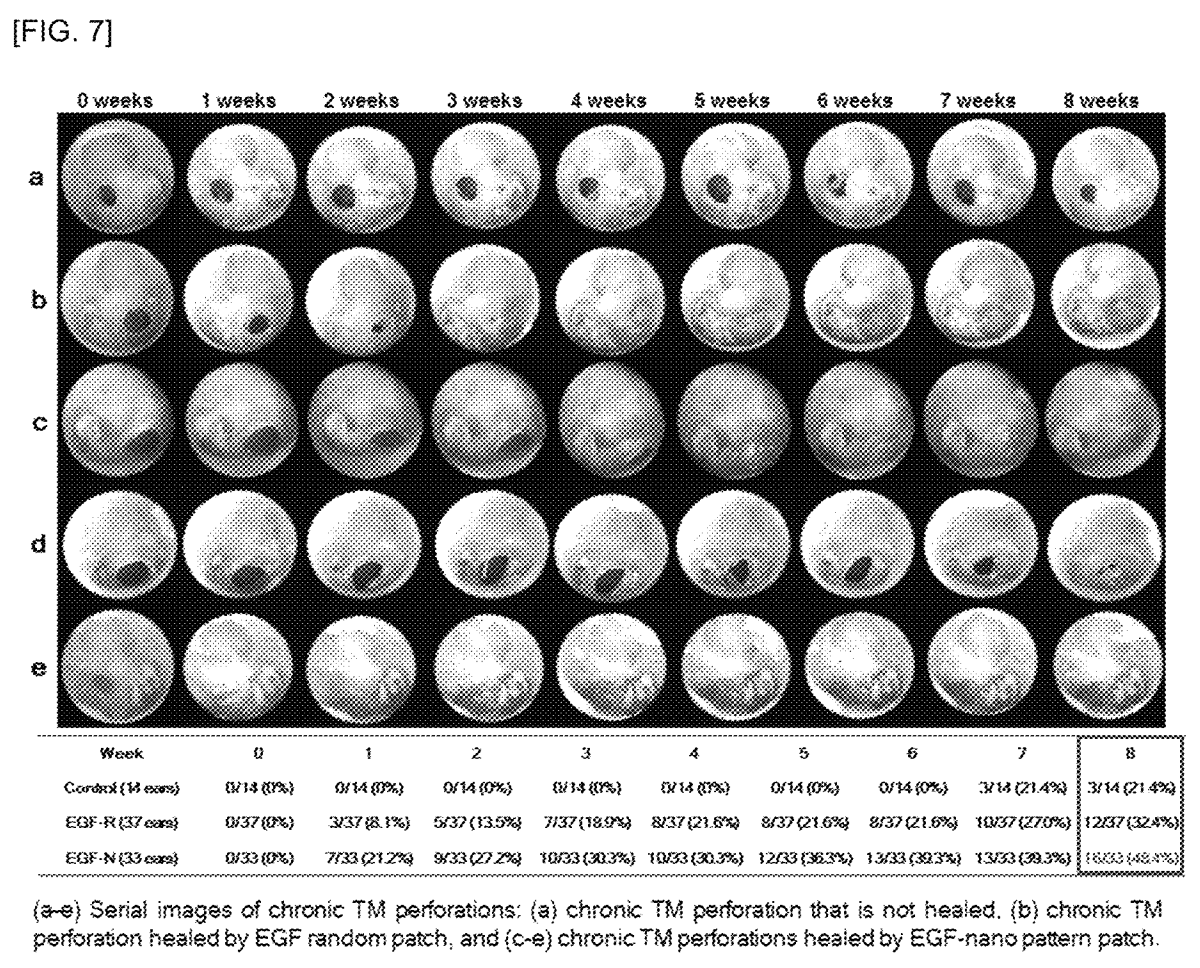

| Week | 0 | 1 | 2 | 3 | 4 | 5 | 6 | 7 | 8 |
|---|---|---|---|---|---|---|---|---|---|
| Control (14 ears) | 0/14 (0%) | 0/14 (0%) | 0/14 (0%) | 0/14 (0%) | 0/14 (0%) | 0/14 (0%) | 0/14 (0%) | 0/14 (0%) | 3/14 (21.4%) | 3/14 (21.4%) |
| EGF-R (37 ears) | 0/37 (0%) | 3/37 (8.1%) | 5/37 (13.5%) | 7/37 (18.9%) | 8/37 (21.6%) | 8/37 (21.6%) | 8/37 (21.6%) | 10/37 (27.0%) | 12/37 (32.4%) |
| EGF-N (33 ears) | 0/33 (0%) | 7/33 (21.2%) | 9/33 (27.2%) | 10/33 (30.3%) | 10/33 (30.3%) | 12/33 (36.3%) | 13/33 (39.3%) | 13/33 (39.3%) | 18/33 (46.3%) |

(a-e) Serial images of chronic TM perforations: (a) chronic TM perforation that is not healed, (b) chronic TM perforation healed by EGF random patch, and (c-e) chronic TM perforations healed by EGF-nano pattern patch.

[FIG. 8]
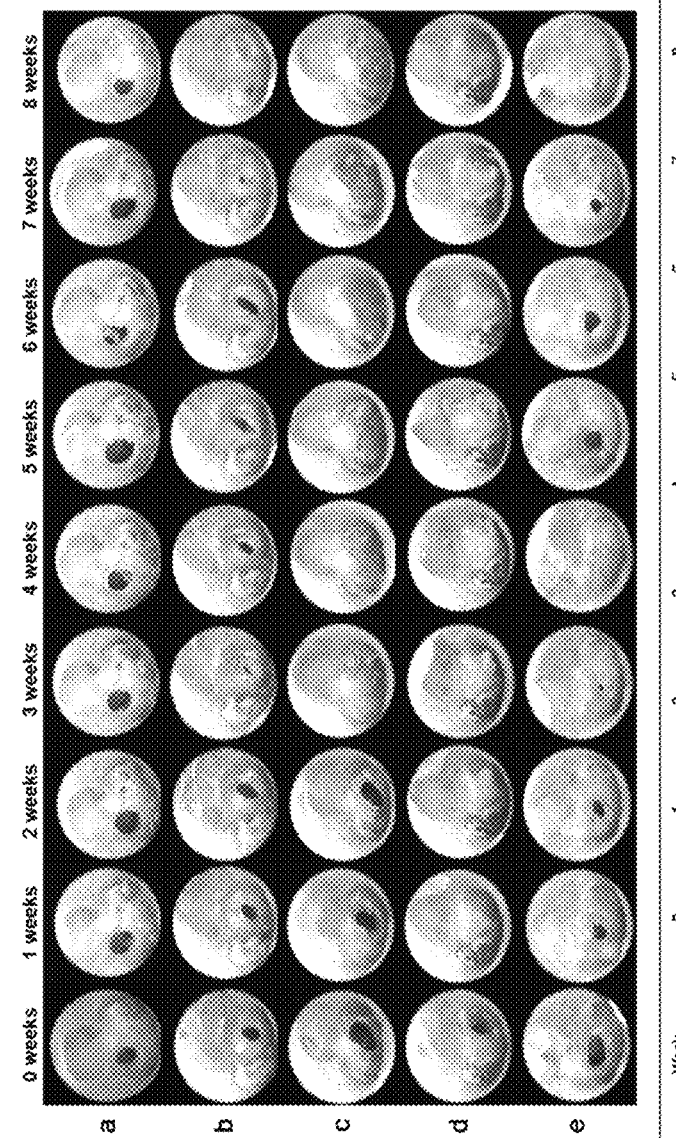
| Week | 0 | 1 | 2 | 3 | 4 | 5 | 6 | 7 | 8 |
|---|---|---|---|---|---|---|---|---|---|
| Control (14 ears) | 0/14 (0%) | 0/14 (0%) | 0/14 (0%) | 0/14 (0%) | 0/14 (0%) | 0/14 (0%) | 0/14 (0%) | 2/14 (14.2%) | 2/14 (14.2%) |
| IGFBP-2_R (18 ears) | 0/18 (0%) | 3/18 (16.6%) | 4/18 (22.2%) | 4/18 (22.2%) | 4/18 (22.2%) | 4/18 (22.2%) | 4/18 (22.2%) | 4/18 (22.2%) | 5/18 (27.7%) |
| IGFBP-2_N (21 ears) | 0/21 (0%) | 4/21 (19.0%) | 4/21 (19.0%) | 5/21 (23.8%) | 5/21 (23.8%) | 5/21 (23.8%) | 5/21 (23.8%) | 5/21 (23.8%) | 7/21 (33%) |
(a-e) Serial images of chronic TM perforations: (a) chronic TM perforation that is not healed, (b) chronic TM perforation healed by IGFBP-2 random patch, and (c-e) chronic TM perforations healed by IGFBP-2-nano pattern patch.*, p<0.05, Mann-Whitney U test

PCL PATCH TISSUE REGENERATION SCAFFOLD AND METHOD FOR MANUFACTURING SAME

CROSS REFERENCE TO PRIOR APPLICATIONS

This application is a Continuation Application of U.S. patent application Ser. No. 16/317,028 filed Mar. 25, 2019, which is a National Stage Application of PCT International Patent Application No. PCT/KR2017/002262 filed on Mar. 2, 2017, under 35 U.S.C. § 371, which claims priority to Korean Patent Application Nos. 10-2016-0088071 filed Jul. 12, 2016 and 10-2017-0018835 filed Feb. 10, 2017, respectively, which are all hereby incorporated by reference in their entirety.

TECHNICAL FIELD

The present invention relates to a PCL patch tissue regeneration scaffold and a method of preparing the same, and more particularly, to a polycaprolactone (PCL) patch tissue regeneration scaffold having a growth factor release type and a method of preparing the same.

BACKGROUND ART

Chronic otitis media (chronic tympanic perforation) is one of the most common causes of hearing damage in the otolaryngology area, in which the perforation of the tympanic membrane continues, however, most of the therapeutic methods still rely on surgical methods (tympanum regeneration).

The perforation of the tympanic membrane can be largely divided into acute and chronic. Acute tympanic perforation is likely to be regenerated naturally if the perforation size is not large, however, most chronic tympanic perforation (chronic otitis media) of at least 3 months old, is not treated naturally, and as it gets older, it can induce complications such as otorrhea, pyopoiesis, hearing loss, facial nerve paralysis or brain abscess.

To treating chronic otitis media, it is generally necessary to use a surgical method called tympanum regeneration, which is costly, requires complicated surgery for an operation time of 1 hour or more and anesthesia, hospitalization, and has a problem for recurrence rate of at least 10%.

According to the National Statistical Office, from year 2009 to 2013, the number of patients with tympanitis is estimated to be about 1.7 million, and the cost of medical treatment has reported about 170 billion won.

Many methods have been studied to overcome the problems of these surgical methods, the most classic of which is the paper patch technique. In other words, it is a treatment that allows marginal cells of tympanic perforation to use a paper patch as a support by cutting and pasting a paper patch on the perforation site. Generally, it is effective for small perforation of acute tympanic perforation, but it has no effect on chronic tympanic perforation. In other words, non-biocompatible materials cause inflammation and the success rate is less than 10%.

In addition to the paper patch technique, during a patch-type scaffold for treating chronic tympanic perforation, chitosan patches containing growth factors was produced and then applied to a chronic animal model to confirm the therapeutic effect. Growth factors were supported on the chitosan patch so as to have a sustained release and it was confirmed that the cure rate was high in the animal model with chronic tympanic perforation. The epidermal growth factor (hereinafter, referred to as 'EGF') supported on the chitosan patch is known to be a factor affecting the proliferation of stem cells, and it has been reported that a patch supporting the same stimulates stem cells remaining in the margin of the tympanic perforation to affect chronic tympanic perforation treatment. However, since the chitosan patch has not been approved by the FDA of the US Food and Drug Administration, various attempts have not been made to easily apply it to clinical practice.

All cells in the human body are in various environments provided by the extracellular matrix (ECM), and the extracellular matrix has been reported to have each specific nanostructures. Recent studies have shown that in vitro experiments can control cell morphology, mobility, and function by nanostructures of the substrate surface on which cells was adhered and grown. Thus, in the case of the tympanic tissue, it is suggested that the tympanic stem cell may change its shape, mobility and function in response to the shape or arrangement of the nanostructure, if the proper nano-environment is provided.

Electrospinning is one of the easiest methods to produce nanofibers, which can produce nanofibers that are uniform, continuous and can exhibit various properties depending on the composition ratio. At this time, the portion in which the nanofibers spun by the electrospinning method are obtained is called a collector, and the characteristics of the nanofibers obtained according to the collector shape can be controlled. Through active research at home and abroad, we have found that cell characteristics are regulated in nanostructures obtained by electrospinning.

However, there is no method for manufacturing a spindle-shaped tissue regeneration scaffold by electrospinning a biodegradable and biocompatible polymer that can be used for drug delivery and various medical field researches.

DISCLOSURE

Technical Problem

It is an object of the present invention to provide a PCL patch tissue regeneration scaffold which can be used as a non-surgical treatment method of chronic tympanic perforation, which is simple and efficient and has a low recurrence rate, and a method of preparing the same.

Technical Solution

In order to solve the above problems, the present invention provides a method of preparing PCL patch tissue regeneration scaffold comprising: preparing solution by adding polycaprolactone (PCL) and an acid to an organic solvent and stirring; preparing an electrospinning solution by adding a growth factor to the solution and stirring; and collecting nanofibers arranged in a spindle shape on a collector by connecting the electrospinning solution prepared to a syringe pump and operating the electrospinning device.

Also, the present invention provides a method of preparing PCL and PEG patch tissue regeneration scaffold comprising: preparing polycaprolactone-polyethylene glycol copolymer solution by adding polycaprolactone (PCL) and polyethylene glycol (PEG) and an acid to an organic solvent and stirring; preparing an electrospinning solution by adding a growth factor to the solution and stirring; and collecting nanofibers arranged in a spindle shape on a collector by connecting the electrospinning solution prepared to a syringe pump and operating the electrospinning device.

In addition, the present invention provides a PCL patch tissue regeneration scaffold comprising polycaprolactone as a nanofiber arranged in a spindle shape.

In addition, the present invention provides a PCL and PEG patch tissue regeneration scaffold comprising polycaprolactone and polyethylene glycol as a nanofiber arranged in a spindle shape.

Furthermore, the present invention provides a composition for preventing or treating chronic tympanic perforation, comprising the PCL patch tissue regeneration scaffold.

In addition, the present invention provides a composition for preventing or treating chronic tympanic perforation, comprising the PCL and PEG patch tissue regeneration scaffold.

Advantageous Effects

The PCL patch tissue regeneration scaffold according to the present invention can be useful for the treatment of chronic tympanic perforation, and especially can reduce the proportion of surgery and have a high recovery of eardrum in a surgical-dependent treatment for chronic tympanic perforation. In addition, PCL patch tissue regeneration scaffolds can be used for regeneration and treatment of damaged tissues, and various tissue regenerated supports can be developed and applied by simulating the tissue structure of other parts of the human body.

DESCRIPTION OF DRAWINGS

FIG. 1 shows a bottom plate design view of the collector (a); a view of placing a columnar collector on bottom plate of the collector bottom plate (b); design of a metal column with one sharp end to be attached to the bottom plate of the collector (c); and a collect for electrospinning for fabrication of a spindle-shaped pattern patch in which all the components combined and modeled (d).

FIG. 2 shows an electron microscope image of the eloectrospun PCL patch having a spindle-type and a photograph of a spindle-type PCL patch at 200× magnifications (a); a photograph of a spindle-type PCL patch at 3000× magnifications (b); a photograph of spindle-type PCL patch 300,000× magnifications (c); and a photograph measuring the thickness of the nanofiber strand from image analysis of a photograph at 300,000× magnifications (d).

FIG. 3 shows an electron microscope image of the eloectrospun PCL and PEG patch having a spindle-type and a photograph of a spindle-type PCL and PEG patch at 200× magnifications (a); a photograph of a spindle-type PCL and PEG patch at 3000× magnifications (b); a photograph of spindle-type PCL and PEG patch 300,000× magnifications (c); and a photograph measuring the thickness of the nanofiber strand from image analysis of a photograph at 300,000× magnifications (d).

FIG. 4 is a view showing the morphology of TM cells in a PCL patch support in which EGF is supported.

FIG. 5a and FIG. 5b show the cell proliferation test results of the tympanic membrane stem cell (TM cell) in the spindle-shaped PCL patch prepared by electrospinning and show the result of the proliferation of the tympanic membrane stem cell in the PCL patch in which PCL and IGFBP2 are supported and the result of the proliferation of the tympanic membrane stem cell in the PCL patch in which PCL and EGF are supported, respectively.

FIG. 6 illustrates the cell proliferation test results of the tympanic membrane stem cell (TM cell) in spindle-shaped PCL and PEG patch prepared by electrospinning showing that the result of the proliferation of the tympanic membrane stem cell on the patch prepared according to Example 4 and Comparative Examples 5 to 7.

FIG. 7 illustrates photographs (a to e) of a test group treated with a spindle-shaped PCL patch showing a patch application test results in animal model with chronic tympanic perforation and a table below shows cure rate of a control, EGF-R PCL patch (randomized and containing EGF) and EGF-N PCL patch (spindle-shaped and containing EGF).

FIG. 8 illustrates photographs (a to e) of a test group treated with a spindle-shaped PCL patch showing a patch application test results in animal model with chronic tympanic perforation and a table below shows cure rate of a control, IGFBP-2_R PCL patch (randomized and containing IGFBP) and IGFBP-2_N PCL patch (spindle-shaped and containing IGFBP).

BEST MODE

Hereinafter, the present invention will be described in more detail.

The inventors of the present invention found that the characteristics of the cells can be controlled by adjusting the characteristics of the nanofibers obtained according to the collector shape by electrospinning and in particular, they have completed the present invention by confirming that growth factors supported by PCL patches and PCL patch supports arranged in a spindle shape are effective for treatment of chronic tympanic membrane.

The present invention provides a method of preparing PCL patch tissue regeneration scaffold comprising: preparing solution by adding polycaprolactone (PCL) and an acid to an organic solvent and stirring; preparing an electrospinning solution by adding a growth factor to the solution and stirring; and collecting nanofibers arranged in a spindle shape on a collector by connecting the electrospinning solution prepared to a syringe pump and operating the electrospinning device.

The polycaprolactone is a polyester-based biodegradable polymer polymerized from caprolactone (CL). Polycaprolactone (PCL) is known as a highly biodegradable and biocompatible polymer, and thus can be used for drug delivery and various medical field researches.

In a step of preparing the solution, polycaprolactone and an acid may be added to the organic solvent and then stirred at a speed of 200 to 500 rpm for 24 to 48 hours, but it is not limited thereto.

The concentration of the polycaprolactone in the organic solvent may be 70 to 90 mg/ml, but it is not limited thereto.

The organic solvent may be any one selected from the group consisting of 2,2,2-trifluoroethanol, chloroform, dichloromethane, tetrahydrofuran, dimethylformamide and dimethylsulfoxide, but it is not limited thereto.

The acid may be any one selected from the group consisting of acetic acid, formic acid, propionic acid and lactic acid, but it is not limited thereto.

The growth factor is any one selected from the group consisting of epithelial growth factor (EGF), fibroblast growth factor (FGF), insulin positive growth factor binding protein (IGFBP) and combination thereof, but it is not limited thereto.

The epithelial growth factor (EGF) promotes the synthesis of DNA, RNA, protein, hyaluronic acid and fibronectin. The EGF is found at the early stage of healing of the tympanic perforation, and the growth factor in which EGF is bound with heparin may play an important role in healing of the tympanic perforation.

The fibroblast growth factor (FGF) can help migration of the fibroblast and proliferate and regenerate cells.

The insulin positive growth factor binding protein (IG-FBP) may inhibit apoptosis and promote growth or differentiation depending on the intracellular matrix.

In a step of preparing the electrospinning solution, the growth factor of 0.16 to 16 µg/ml may be added to the solution, but it is not limited thereto.

In a step of preparing an electrospinning solution, the growth factor may be added to the solution, followed by stirring at 0 to 10° C. for 20 to 30 minutes, but it is limited thereto.

In a step of collecting the nanofibers, a electrospinning may be operated by connecting the electrospinning solution prepared to a syringe pump and discharging at a rate of 0.2 to 3.0 µl/hr, but it is not limited thereto.

The nanofibers may have 200 to 800 nm of an average thickness, but it is not limited thereto.

The collector may be in a cylindrical form for receiving needles therein, but it is not limited thereto.

Referring to FIG. 1, the collector collects charged nanofibers, and is composed of a copper pipe having excellent conductivity and a metal needle having a sharp end at the center thereof.

Also, the present invention provides a method of preparing PCL and PEG patch tissue regeneration scaffold comprising: preparing polycaprolactone-polyethylene glycol copolymer solution by adding polycaprolactone (PCL) and polyethylene glycol (PEG) and an acid to an organic solvent and stirring; preparing an electrospinning solution by adding a growth factor to the solution and stirring; and collecting nanofibers arranged in a spindle shape on a collector by connecting the electrospinning solution prepared to a syringe pump and operating the electrospinning device.

In a step of preparing the solution, polycaprolactone and polyethylene glycol and an acid may be added to the organic solvent and then stirred at a speed of 200 to 500 rpm for 24 to 48 hours, but it is not limited thereto.

The concentration of the polycaprolactone in the organic solvent may be 100 to 160 mg/ml, but it is not limited thereto.

The concentration of the polyethylene glycol in the organic solvent may be 40 to 100 mg/ml, but it is not limited thereto.

The organic solvent may be any one selected from the group consisting of 2,2,2-trifluoroethanol, chloroform, dichloromethane, tetrahydrofuran, dimethylformamide and dimethylsulfoxide, but it is not limited thereto.

The acid may be any one selected from the group consisting of acetic acid, formic acid, propionic acid and lactic acid, but it is not limited thereto.

The growth factor is any one selected from the group consisting of epithelial growth factor (EGF), fibroblast growth factor (FGF), insulin positive growth factor binding protein (IGFBP) and combination thereof, but it is not limited thereto.

In a step of preparing the electrospinning solution, the growth factor of 16 to 16 µg/ml may be added to the solution, but it is not limited thereto.

In a step of preparing an electrospinning solution, the growth factor may be added to the solution, followed by stirring at 0 to 10° C. for 20 to 30 minutes, but it is limited thereto.

In a step of collecting the nanofibers, a electrospinning may be operated by connecting the electrospinning solution prepared to a syringe pump and discharging at a rate of 0.2 to 3.0 µl/hr, but it is not limited thereto.

The nanofibers may have 200 to 800 nm of an average thickness, but it is not limited thereto.

The collector may be in a cylindrical form for receiving needles therein, but it is not limited thereto.

In addition, the present invention provides a PCL patch tissue regeneration scaffold comprising polycaprolactone as a nanofiber arranged in a spindle shape.

The PCL patch tissue regeneration scaffold may further comprise a growth factor, but it is not limited thereto.

The PCL patch tissue regeneration scaffold may comprise polycaprolactone and a growth factor in a weight ratio of $10^4$ to $10^6$:1, but it is not limited thereto.

The growth factor may be any one selected from the group consisting of epithelial growth factor (EGF), fibroblast growth factor (FGF), insulin positive growth factor binding protein (IGFBP) and combination thereof, but it is not limited thereto.

The nanofibers may have 200 to 800 nm of an average thickness, but it is not limited thereto.

In addition, the present invention provides a PCL and PEG patch tissue regeneration scaffold comprising polycaprolactone and polyethylene glycol as a nanofiber arranged in a spindle shape.

The PCL and PEG patch tissue regeneration scaffold may further comprise growth factors, but it is not limited thereto.

The PCL and PEG patch tissue regeneration scaffold may comprise polycaprolactone and a growth factor in weight ratio of $(7×10^4-7×10^6)$:1, but it is not limited thereto.

The PCL and PEG patch tissue regeneration scaffold may comprise polyethylene glycol and a growth factor in weight ratio of $(3×10^4-3×10^6)$:1, but it is not limited thereto.

The PCL and PEG patch tissue regeneration scaffold may comprise polycaprolactone and polyethylene glycol in weight ratio of (2-4):1, but it is not limited thereto.

The growth factor may be any one selected from the group consisting of epithelial growth factor (EGF), fibroblast growth factor (FGF), insulin positive growth factor binding protein (IGFBP) and combination thereof, but it is not limited thereto.

The nanofibers may have 200 to 800 nm of an average thickness, but it is not limited thereto.

In addition, the present invention provides a composition for preventing or treating chronic tympanic perforation, comprising the PCL patch tissue regeneration scaffold.

Furthermore, the present invention provides a composition for preventing or treating chronic tympanic perforation, comprising the PCL and PEG patch tissue regeneration scaffold.

The composition may be a pharmaceutical composition or a health functional food, but is not limited thereto.

The pharmaceutical compositions may be formulated in the form of oral preparations such as powders, granules, tablets, capsules, suspensions, emulsions, syrups, aerosols and the like, external applications, suppositories and sterilized injection solutions according to a conventional method.

In the case of formulation, a diluent or excipient such as commonly used filler, an extender, a binder, a wetting agent, a disintegrant, a surfactant or the like is used. Solid formulations for oral administration include tablets, pills, powders, granules, capsules, etc., which may contain at least one excipient such as starch, calcium carbonate, sucrose or lactose, gelatin, and the like.

In addition to simple excipients, lubricants such as magnesium stearate and talc are also used. Examples of the liquid formulations for oral administration include suspensions, solutions for internal use, emulsions, syrups and the like and in addition to water and liquid paraffin which are commonly used simple diluents, various excipients such as wetting agents, sweeteners, fragrances and preservatives and the like may be included.

Formulations for parenteral administration include sterile aqueous solutions, non-aqueous solutions, suspensions, emulsions, freeze-dried preparations, and suppositories. Examples of the non-aqueous solution and the suspension include propylene glycol, polyethylene glycol, vegetable oil such as olive oil, injectable ester such as ethyl oleate, and the like. As the base of the suppository, witepsol, macrogol, tween 61, cacao butter, laurinum, glycerogelatin and the like can be used.

The used amount of the compound which is an active ingredient of the pharmaceutical composition may vary depending on the age, sex, body weight and disease of the patient, but 0.001 to 100 mg/kg, preferably 0.01 to 10 mg/kg, may be administered once to several times per day.

The dosage of the pharmaceutical composition may be increased or decreased according to the route of administration, degree of disease, sex, weight, age, and the like. Accordingly, the dosage amounts do not limit the scope of the invention in any aspect.

The pharmaceutical composition may be administered to mammals such as rats, mice, livestock, humans, and the like in a variety of routes. All modes of administration may be expected, for example, by oral, rectal or intravenous, intramuscular, subcutaneous, intratracheal inhalation, intrauterine dural or intracerebroventricular injections.

Also, the health functional food may be provided in the form of powder, granules, tablets, capsules, syrups or beverages and the health functional food may be used together with other food or food additives other than the active ingredient of the present invention, and can be suitably used according to the conventional methods. The amount of the active ingredient to be mixed can be appropriately determined according to its use purpose, for example, prevention, health or therapeutic treatment.

The effective dose of the compound contained in the health functional food may be used in accordance with the effective dose of the pharmaceutical composition, but may be less than the above range for health and hygiene purposes or long-term intake for health control purposes. It is clear that the active ingredient can be used in an amount of more than the above range because it has no problem in terms of safety.

There is no particular limitation on the kind of the health functional food and examples of the health functional food include meat, sausage, bread, chocolate, candy, snack, confectionery, pizza, ramen and other noodles, gums, dairy products including ice cream, various soup, beverages, teas, drinks, alcoholic beverages, and vitamin complex, etc.

Hereinafter, the present invention will be described in more detail with reference to the following examples. However, the present invention is not limited by these examples.

EXAMPLE 1

The distance between an end of the needle of the 22 gage and the collector was fixed at 10 cm, and a voltage of 18 kV was generated by the voltage generator.

A solution was prepared by adding 160 mg of polycaprolactone (PCL) and 40 μl of acetic acid to 2 ml of trifluoroethanol (TFE). The solution was then prepared by stirring at a speed of 300 rpm for 24 to 48 hours so that the PCL could be completely dissolved in the TFE.

After confirming that the PCL was completely dissolved, 1.6 μg of EGF was added to the solution. Thereafter, an electrospinning solution was prepared by stirring at 4° C. for 20 minutes so that EGF could be mixed well with PCL.

The prepared electrospinning solution was put in a syringe and connected to a syringe pump and was spun at a rate of 0.6 μl/hr.

As shown in FIG. 1, a collector made of a copper pipe having good conductivity and a metallic needle with a sharp middle end was used so as to collect in the form of a spindle-shaped pattern patch and a condition was controlled so as to generate an electric field of 1.6 kV/cm and to operate the electrospinning device thereby preparing a PCL patch tissue regeneration scaffold arranged in a spindle shape. Hereinafter, the PCL patch tissue regeneration scaffold prepared according to Example 1 was designated as 'EGF-A'.

EXAMPLE 2

A PCL patch tissue regeneration scaffold arranged in a spindle shape was prepared under the same conditions as in Example 1 except that 1.6 μg of IGFBP was added instead of EGF. Hereinafter, the PCL patch tissue regeneration scaffold prepared according to Example 2 was designated as 'IGFBP-A'.

EXAMPLE 3

A PCL patch tissue regeneration scaffold arranged in a spindle shape was prepared under the same conditions as in Example 1, except that 1.6 μg and 1.6 μg of EGF and IGFBP were added, respectively. The PCL patch tissue regeneration scaffold prepared according to Example 3 was designated as 'EGF/IGFBP-A'.

EXAMPLE 4

The distance between an end of the needle of the 22 gage and the collector was fixed at 10 cm, and a voltage of 18 kV was generated by the voltage generator.

A solution was prepared by adding 280 mg of polycaprolactone (PCL, MW: 80,000, Sigma Aldrich) and 120 mg of polyethylene glycol (PEG, MW: 3,350, Sigma Aldrich) and 40 μl of acetic acid (Sigma Aldrich) to 2 ml of trifluoroethanol (TFE). The solution was then prepared by stirring at a speed of 300 rpm for 24 to 48 hours so that the PCL and PEG could be completely dissolved in the TFE.

After confirming that PCL and PEG were completely dissolved, 4 μg of EGF was added to the solution. Thereafter, an electrospinning solution was prepared by stirring at 4° C. for 20 minutes so that EGF could be mixed well with PCL and PEG.

The prepared electrospinning solution was put in a syringe and connected to a syringe pump and was spun at a rate of 0.6 μl/hr.

As shown in FIG. 1, a collector made of a copper pipe having good conductivity and a metallic needle with a sharp middle end was used so as to collect in the form of a spindle-shaped pattern patch and a condition was controlled so as to generate an electric field of 1.6 kV/cm and to operate the electrospinning device thereby preparing a PCL and PEG patch tissue regeneration scaffold arranged in a spindle shape. Hereinafter, the PCL and PEG patch tissue regeneration scaffold prepared according to Example 4 was designated as 'PCL/PEG/EGF-A'.

COMPARATIVE EXAMPLE 1

The procedure was performed under the same condition as the Example 1 except that EGF, a growth factor, was not added and a collector commonly used in electrospinning was used and hereinafter it is designated as 'PCL-R'.

COMPARATIVE EXAMPLE 2

The procedure was performed under the same condition as the Example 1 except that EGF, a growth factor, was not added and hereinafter it is designated as 'PCL-A'.

COMPARATIVE EXAMPLE 3

The procedure was performed under the same condition as the Example 1 except that a collector commonly used in electrospinning was used and hereinafter it is designated as 'EGF-R'.

COMPARATIVE EXAMPLE 4

The procedure was performed under the same condition as the Example 2 except that a collector commonly used in electrospinning was used and hereinafter it is designated as 'IGFBP-R'.

COMPARATIVE EXAMPLE 5

The procedure was performed under the same condition as the Example 4 except that a collector commonly used in electrospinning was used and hereinafter it is designated as 'PCL/PEG/EGF-R'.

COMPARATIVE EXAMPLE 6

The procedure was performed under the same condition as the Example 4 except that EGF, a growth factor, was not added and a collector commonly used in electrospinning was used and hereinafter it is designated as 'PCL/PEG-R'.

COMPARATIVE EXAMPLE 7

The procedure was performed under the same condition as the Example 4 except that EGF, a growth factor, was not added and hereinafter it is designated as 'PCL/PEG-A'.

Experimental Example 1 Morphological Analysis of a Spindle-Shaped PCL Patch Support for Tympanic Membrane Regeneration Scanning electron microscopy (SEM) was performed using a scanning electron microscope (SUPRA, Carl Zeiss, Germany) to analyze the surface characteristics of the spindle-shaped PCL patch support for regenerating the tympanic membrane prepared under the various spinning conditions.

FIG. 2(a) to FIG. 2(d) show scanning electron microscope images of a spindle-shaped PCL patch obtained from a cylindrical collector housing a needle inside thereof. Referring to FIG. 2(a), it can be seen that each nanofiber strand was oriented in the center through a photograph at 200× magnifications.

FIG. 2(b) and FIG. 2(c) were obtained by randomly enlarging a specific portion of the sample. It can be confirmed that most of the nanofiber strands extend straight.

Referring to FIG. 2(d), the thickness of each nanofiber strand was not more than 300 nm.

Experimental Example 2 Morphological Analysis of Spindle-Shaped PCL and PEG Patch Supports for Tympanic Membrane Regeneration Scanning electron microscopy (SEM) was performed using a scanning electron microscope (SUPRA, Carl Zeiss, Germany) to analyze the surface characteristics of the spindle-shaped PCL and PEG patch support for regenerating the tympanic membrane prepared under the various spinning conditions.

In addition, FIG. 3(a) to FIG. 3(d) show scanning electron microscope images of a spindle-shaped PCL and PEG patch obtained from a cylindrical collector housing a needle inside thereof.

Referring to FIG. 3(a), it can be seen that each nanofiber strand was oriented in the center through a photograph at 200× magnifications.

In addition, FIG. 3(b) and FIG. 3(c) were obtained by randomly enlarging a specific portion of the sample. It can be confirmed that most of the nanofiber strands extend straight.

Furthermore, referring to FIG. 3(d), the thickness of each nanofiber strand was not more than 300 nm.

Experimental Example 3 In Vitro Assay of PCL Nano-Pattern Patch

Rat fibroblasts and rat fibroblast passage 2 taken from a tympanic membrane of rat (provided by department of otorhinolaryngology of Ajou University, referred to as "TM cells") were used for in vitro assay. The frozen TM cells were thawed and then cultured in a 5% $CO_2$ incubator at 37° C. for 7 to 10 hours in a medium prepared by mixing DMEM low glucose, 10% FBS (Fatal Bovine Serum) and 1% penicillin. After confirming that the culture density of TM cells was confluent, they were separated on a culture plate with trypsin EDTA.

At this time, in vitro assay was performed for the experimental group consisted of spindle-shaped patch containing EGF prepared in Example 1 (EGF-A), nano-pattern patch in which the PCL prepared in Comparative Example 1 was spun in the form of a nonwoven fabric (PCL-R), nano-pattern patch arranged in the spindle shape prepared in Comparative Example 2 (PCL-A) and the random patch containing EGF prepared in Comparative Example 3 (EGF-R).

Then, the four types of patches were prepared in a circle having a diameter of 6 mm on a 96-well plate and fixed on each plate. Each 96 well plate was seeded with 1×10³ TM cells per well.

Cell activity was measured by WST test at intervals of 1 day, 3 days, and 5 days. Also, the above-mentioned procedure was repeated by including the IGFBP prepared in Example 2 in the patch.

The appearance of TM cells attached to the patches containing EGF according to Example 1 was analyzed by fluorescence microscopy. This example was conducted to investigate the role of EGF-containing nanofibers in the shape of EGF and to predict the effect of patterns on nano-pattern patches.

Referring to FIG. 4, Random refers to patches randomly spun, Aligned refers to patches arranged in a spindle shape, w/o EGF means no EGF and w EGF means EGF is contained.

Referring to FIG. 4, the elongated shape of TM cells was observed in a patch containing EGF. It was also confirmed that the spindle-shaped pattern was arranged in the direction of the center (Centroid), and this phenomenon was observed more evident in the elongated experimental group containing the EGF.

FIG. 5a and FIG. 5b show the results of confirming cell proliferation by culturing the tympanic membrane stem cells on a 5-day-old patch to measure the activity of the cells, and similar results were observed in PCL patches containing EGF and IGFBP prepared according to Example 1 and Example 2. In both tests, no significant difference was observed on days 1 and 3, and the difference was not significant until day 5 in both experiments. That is, it was observed that the cell proliferation on the spindle-shaped PCL patch containing EGF and IGFBP prepared according to Example 1 and Example 2 was the most active.

Experimental Example 4 In Vitro Assay of PCL and PEG Nano-Pattern Patch

Rat fibroblast passage 2 taken from a tympanic membrane of rat (provided by department of otorhinolaryngology of Ajou University, referred to as "TM cells") was used for in vitro assay. The frozen TM cells were thawed and then cultured in a 5% $CO_2$ incubator at 37° C. for 7 to 10 hours in a medium prepared by mixing DMEM low glucose, 10% FBS (Fatal Bovine Serum) and 1% penicillin. After confirming that the culture density of TM cells was confluent, they were separated on a culture plate with trypsin EDTA.

At this time, in vitro assay was performed for the experimental group consisted of PCL and PEG spindle-shaped nano-pattern patch containing EGF (Example 4, PCL/PEG/EGF-A), nano-patch in which PCL and PEG containing EGF was spun in nonwoven fabric (Comparative Example 5, PCL/PEG/EGF-R), nano-patch in which PCL and PEG without EGF was spun in nonwoven fabric (Comparative Example 6, PCL/PEG-R) and PCL and PEG spindle-shaped spindle-shaped nano-pattern patch without EGF (Comparative Example 7, PCL/PEG-A).

Then, the four types of patches were prepared in a circle having a diameter of 6 mm on a 96-well plate and fixed on each plate. Thereafter, $1×10^3$ TM cells per well was dispensed into each 96 well plate.

Thereafter, cell activity was measured by WST test at intervals of 1 day, 3 days, and 7 days.

FIG. 6 shows the results of confirming cell proliferation in the manner of measuring cell activity by culturing the tympanic membrane stem cells on a patch for 1 day, 3 days and 7 days.

Referring to the drawings, in PCL and PEG patches containing EGF prepared according to Example 4 and Comparative Example 5, and PCL and PEG patches without EGF prepared according to Comparative Example 6 and Comparative Example 7, the cell adhesion and proliferation were observed to be rapid on the patch containing EGF on day 1, day 3 and day 7.

However, comparing the PCL and PEG patch containing EGF prepared according to Example 4 and Comparative Example 5, the cell adhesion was excellent in the patch prepared according to Comparative Example 5, but considering that PCL and PEG patch containing EGF prepared according to Example 4 exhibited a better tendency, cell proliferation on the 7th day on the PCL and PEG nano-pattern patch containing EGF prepared according to Example 4 exhibited rapid cell proliferation.

Experimental Example 5 Application of PCL Patch Support to Animal Model of Chronic Tympanic Membrane A model for chronic tympanic membrane perforation was fabricated in Sprague-Dawley rats using Choung's COM mode 1 (Choi S J, et al. TERM 2011) for tympanic membrane with perforation lasting more than 8 weeks. The experimental group was fused with a spindle patch and a random patch containing EGF and IGFBP-2, and the no treatment was given for control group. The size of the tympanic membrane perforation was measured by measuring the size change in every week by marking the relative ratio of the perforation size (%) to the pars tensa of the tympanic membrane in a photograph taken using an endoscope. The cure rates of the tympanic membrane were compared by observing it for 8 weeks after patch attachment.

After this, the effect of treatment by patch was observed for 8 weeks. When the patch fell off during observation, a new patch was attached and managed. In the last 8th week, the patch was removed and the puncture site was observed.

FIG. 7 shows the result of applying a PCL patch in a model of a chronic tympanic membrane perforation animal. Each of the orange-colored circle photographs is a photograph of the tympanic membrane of each animal model and dark circles on the lower left of each tympanic membrane indicate the tympanic membrane perforation.

FIG. 7(a) shows the result that the perforation is maintained because the recovery is not performed and FIG. 7(b) to FIG. 7(e) show that the recovery has been made and most of the perforations have disappeared.

In the control group (see FIG. 7(a)) in which no treatment was performed, it was observed that 21.4% (2/14) of the tympanic membrane was recovered. The experimental group to which the EGF random PCL patch prepared in Comparative Example 3 was applied showed a tympanic membrane recovery rate of 32.4% (12/37), and the experimental group to which the EGF spindle-shaped PCL patch prepared in Example 1 was applied showed a tympanic membrane recovery rate of 48.4% (16/33), FIG. 8 shows the result of applying PCL patch in which IGFBP was supported in a chronic tympanic membrane perforation animal model. In the control group without any treatment (see FIG. 8(a)), 14.2% (2/14) of the tympanic membrane was recovered. The experimental group to which the IGFBP random patch prepared by the Comparative Example 4 was applied showed a tympanic membrane recovery rate of 27.7% (5/18), and the experimental group to which the IGFBP spindle-shaped patch prepared according to Example 2 was applied showed a tympanic membrane recovery rate of 35.0% (7/20). It was confirmed that the growth factors (EGF and IGFBP) supported by the PCL patches and the spindle-shaped pattern structure of the patch support were effective in the treatment of chronic tympanic membrane.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A method of treating a chronic tympanic membrane perforation in a subject, comprising:

preparing a spindle-shaped polycaprolactone (PCL) patch tissue regeneration scaffold by: preparing an electrospinning solution by adding the PCL and acetic acid to an organic solvent and stirring, wherein a concentration of the PCL in the organic solvent is 70 to 90 mg/ml;

adding epithelial growth factor (EGF) and insulin growth factor binding protein (IGFBP) to the electrospinning solution and stirring at a temperature between 0° C. and 10° C., wherein the electrospinning solution comprises 0.16 to 16 µg/ml of the EGF and 0.16 to 16 µg/mL of the IGFBP;

and collecting nanofibers on a cylindrical collector housing a single centrally located needle with a sharp end by electrospinning the electrospinning solution through a syringe pump at a flow rate of 0.2 to 3.0 µL/hr while applying 3 voltage of 18 kV across a distance of 10 cm between the single centrally located needle and the cylindrical collector, wherein the collected nanofibers are arranged in a radially aligned pattern converging from a periphery toward the single centrally located needle, thereby forming the spindle-shaped PCL patch tissue regeneration scaffold; and applying the spindle-shaped PCL patch tissue regeneration scaffold to the subject's tympanic membrane perforation of the subject without surgery, whereby the tympanic membrane at the chronic tympanie perforation is regenerated in the subject using the spindle-shaped PCL patch tissue regeneration scaffold loaded with the EGF and the IGFBP.

2. A method of treating a chronic tympanic membrane perforation in a subject, comprising:

preparing a spindle-shaped PCL-PEG patch tissue regeneration scaffold by:

preparing an electrospinning solution by adding polycaprolactone (PCL), polyethylene glycol (PEG), and acetic acid to an organic solvent and stirring to dissolve the polymers, wherein the electrospinning solution comprises PCL at a concentration of 100 to 160 mg/ml and PEG at a concentration of 40 to 100 mg/ml;

adding epithelial growth factor (EGF) and insulin growth factor binding protein (IGFBP) to the electrospinning solution and stirring at a temperature between 0° C. and 10° C., wherein the electrospinning solution comprises 0.16 to 16 µg/ml of the EGF and 0.16 to 16 µg/ml of the IGFBP; and collecting nanofibers on a cylindrical collector housing a single centrally located needle with a sharp end by electrospinning the electrospinning solution through a syringe pump at a flow rate of 0.2 to 3.0 µL/hr while applying a voltage of 18 k kV across a distance of 10 cm between the single centrally located needle and the cylindrical collector, wherein the collected nanofibers are arranged in a radially aligned pattern converging from a periphery toward the single centrally located needle, thereby forming the spindle-shaped PCL-PEG patch tissue regeneration scaffold; and applying the spindle-shaped PCL-PEG patch tissue regeneration scaffold to the tympanic membrane perforation of the subject without surgery; whereby the tympanic membrane perforation is regenerated in the subject using the spindle-shaped PCL-PEG patch tissue regeneration scaffold loaded with the EGF and the IGFBP.

* * * * *